(12) United States Patent
Bailey

(10) Patent No.: US 9,867,537 B2
(45) Date of Patent: Jan. 16, 2018

(54) AUTOMATED DETECTION OF EYE ALIGNMENT

(71) Applicant: OHIO STATE INNOVATION FOUNDATION, Columbus, OH (US)

(72) Inventor: Melissa Diane Bailey, Gahanna, OH (US)

(73) Assignee: Ohio State Innovation Foundation, Columbus, OH (US)

(*) Notice: Subject to any disclaimer, the term of this patent is extended or adjusted under 35 U.S.C. 154(b) by 0 days.

(21) Appl. No.: 14/893,626

(22) PCT Filed: Nov. 7, 2014

(86) PCT No.: PCT/US2014/064555
§ 371 (c)(1),
(2) Date: Nov. 24, 2015

(87) PCT Pub. No.: WO2015/070023
PCT Pub. Date: May 14, 2015

(65) Prior Publication Data
US 2016/0270653 A1 Sep. 22, 2016

Related U.S. Application Data

(60) Provisional application No. 61/901,432, filed on Nov. 7, 2013.

(51) Int. Cl.
*A61B 3/14* (2006.01)
*A61B 3/02* (2006.01)
(Continued)

(52) U.S. Cl.
CPC ............ *A61B 3/113* (2013.01); *A61B 3/0025* (2013.01); *A61B 3/0091* (2013.01); *A61B 3/08* (2013.01);
(Continued)

(58) Field of Classification Search
CPC ... A61B 3/0008; A61B 3/0025; A61B 3/0091; A61B 3/028; A61B 3/08; A61B 3/09;
(Continued)

(56) References Cited

U.S. PATENT DOCUMENTS 2,057,412 A 10/1936 Boyd
2,238,207 A 4/1941 Ames, Jr. et al.
(Continued)

FOREIGN PATENT DOCUMENTS

WO 1988005281 7/1988
WO 2002000105 1/2002
(Continued)

OTHER PUBLICATIONS

Calvin, Helen, Pamela Rupnow, and Theodore Grosvenor. "How good is the estimated cover test at predicting the von Graefe phoria measurement?." Optometry & Vision Science 73.11 (1996): 701-706.
(Continued)

*Primary Examiner* — Jack Dinh
(74) *Attorney, Agent, or Firm* — Meunier Carlin & Curfman LLC

(57) ABSTRACT

An example method for automatically measuring a subject's phoria while the subject fixates on a visual target can include capturing an image of at least one of the subject's eyes using an image capturing device. The image can include a reflection of light from at least one of the subject's eyes. The method can also include analyzing the image to identify a position of the reflection of the light within at least one of the subject's eyes, and determining a phoria measurement based on the position of the reflection of the light within at least one of the subject's eyes.

27 Claims, 12 Drawing Sheets

(51) Int. Cl.
*A61B 3/113* (2006.01)
*A61B 3/08* (2006.01)
*A61B 3/00* (2006.01)
*A61B 3/103* (2006.01)

(52) U.S. Cl.
CPC .............. *A61B 3/085* (2013.01); *A61B 3/103* (2013.01); *A61B 3/14* (2013.01); *A61B 3/145* (2013.01)

(58) Field of Classification Search
CPC ........... A61B 3/103; A61B 3/113; A61B 3/14; A61B 3/15; A61B 3/152; A61B 3/158
USPC ........................................ 351/208, 209, 222
See application file for complete search history.

(56) References Cited

U.S. PATENT DOCUMENTS

| | | |
|---|---|---|
| 2,676,588 A | 4/1954 | Burton |
| 2,986,068 A | 5/1961 | Mandaville |
| 3,879,113 A | 4/1975 | Howland et al. |
| 3,891,311 A | 6/1975 | Fletcher et al. |
| 4,411,501 A | 10/1983 | Tagnon |
| 4,712,895 A | 12/1987 | Kamiyama et al. |
| 5,026,151 A | 6/1991 | Waltuck |
| 5,094,521 A | 3/1992 | Jolson |
| 5,363,154 A | 11/1994 | Galanter |
| 5,757,460 A | 5/1998 | Cockley |
| 6,120,461 A | 9/2000 | Smyth |
| 6,663,242 B1 | 12/2003 | Davenport |
| 7,367,675 B2 | 5/2008 | Maddalena et al. |
| 7,458,686 B2 | 12/2008 | Ikezawa |
| 7,771,051 B2 | 8/2010 | Hirji |
| 7,878,652 B2 | 2/2011 | Chen et al. |
| 8,684,529 B2 | 4/2014 | Johansson et al. |
| 2007/0216867 A1 | 9/2007 | Campbell et al. |
| 2009/0079937 A1 | 3/2009 | Chen et al. |
| 2009/0153796 A1 | 6/2009 | Rabner |
| 2009/0303435 A1 | 12/2009 | Flitcroft et al. |
| 2011/0299034 A1 | 12/2011 | Walsh et al. |
| 2012/0092621 A1 | 4/2012 | Ozaki |
| 2012/0188508 A1 | 7/2012 | Kim et al. |
| 2012/0274905 A1 | 11/2012 | Johansson et al. |
| 2012/0287398 A1 | 11/2012 | Baker |
| 2012/0307203 A1 | 12/2012 | Vendel et al. |
| 2013/0100401 A1 | 4/2013 | Tabor |
| 2013/0235346 A1 | 9/2013 | Huang et al. |

FOREIGN PATENT DOCUMENTS

| | | |
|---|---|---|
| WO | 2012046763 | 4/2012 |
| WO | 2013036629 | 3/2013 |

OTHER PUBLICATIONS

Han, Sang J., et al. "Quantification of heterophoria and phoria adaptation using an automated objective system compared to clinical methods." Ophthalmic and Physiological Optics 30.1 (2010): 95-107.

Hrynchak, Patricia K., Christopher Herriot, and Elizabeth L. Irving. "Comparison of alternate cover test reliability at near in non-strabismus between experienced and novice examiners." Ophthalmic and Physiological Optics 30.3 (2010): 304-309.

Schroeder, Tracy L., et al. "Reliability of and comparisons among methods of measuring dissociated phoria." Optometry & Vision Science 73.6 (1996): 389-397.

International Search Report and Written Opinion of the U.S. International Searching Authority from International Application No. PCT/US2014/064555, dated Apr. 29, 2015, 17 pages.

Non Final Office Action issued in related U.S. Appl. No. 14/950,968, dated Oct. 11, 2016.

Extended European Search Report for Counterpart Application No. 14859789.1 dated Nov. 22, 2016.

Notice of Allowance and Fees Due for Co-Pending U.S. Appl. No. 14/950,968, dated Apr. 27, 2017.

Non-Final Office Action Issued in co-pending U.S. Appl. No. 14/950,755, dated Jun. 16, 2017.

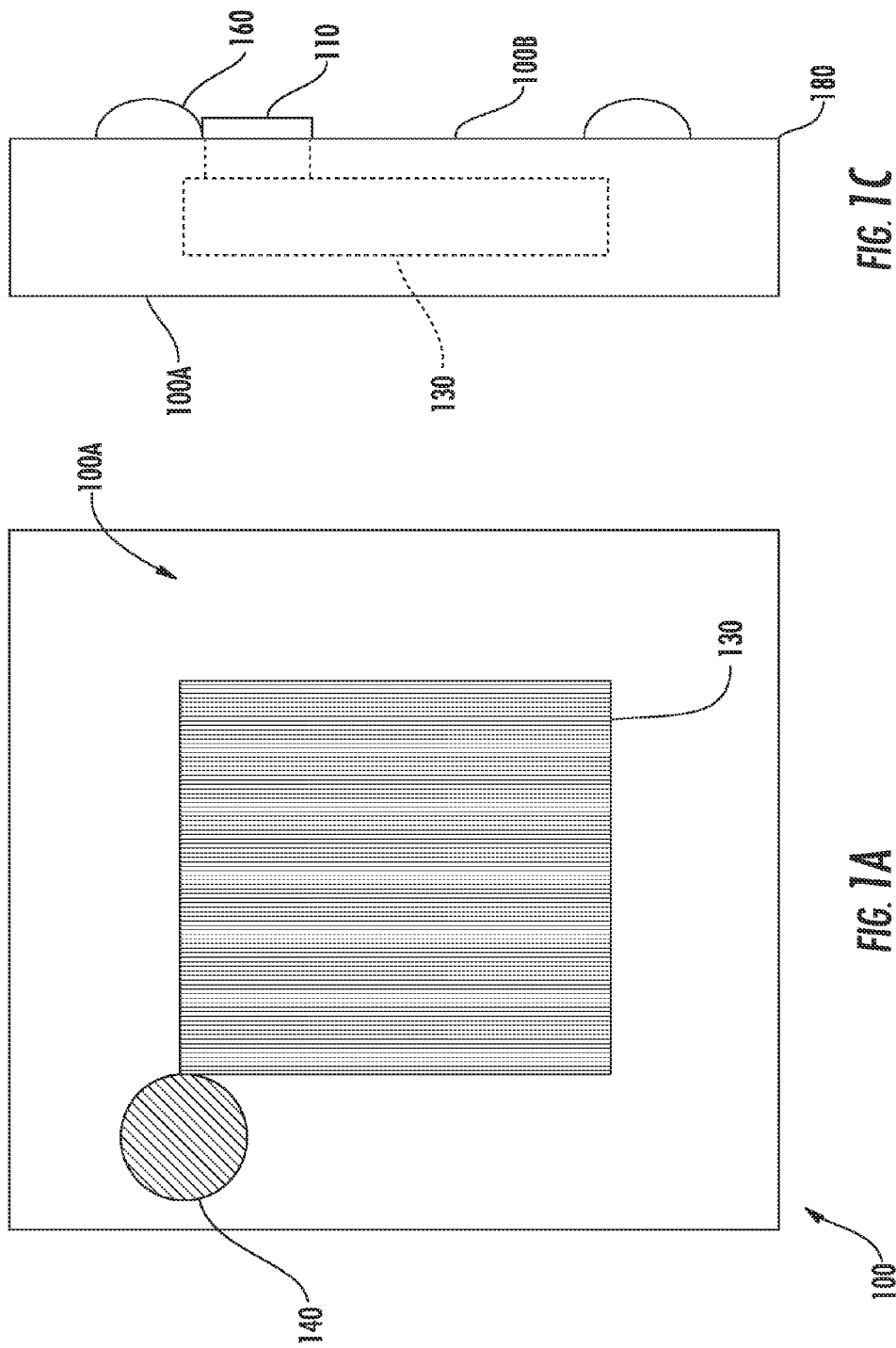

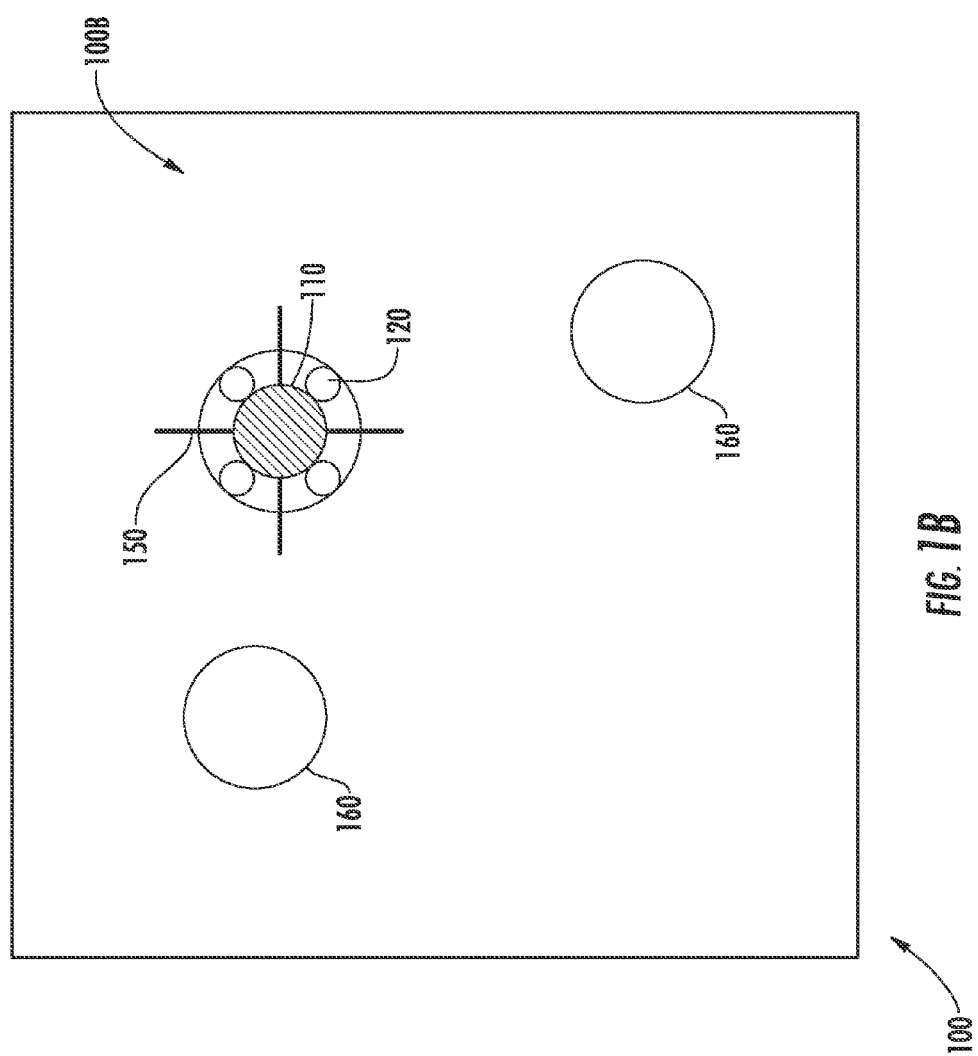

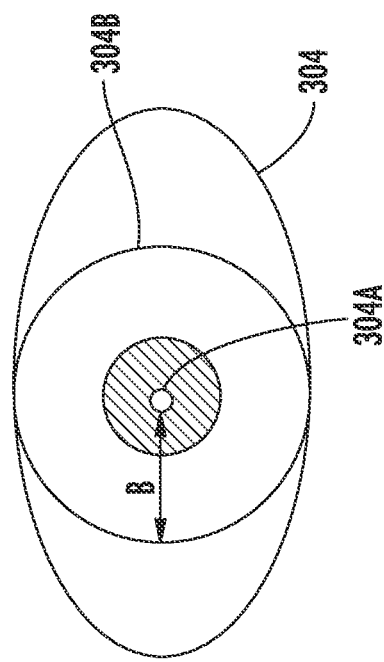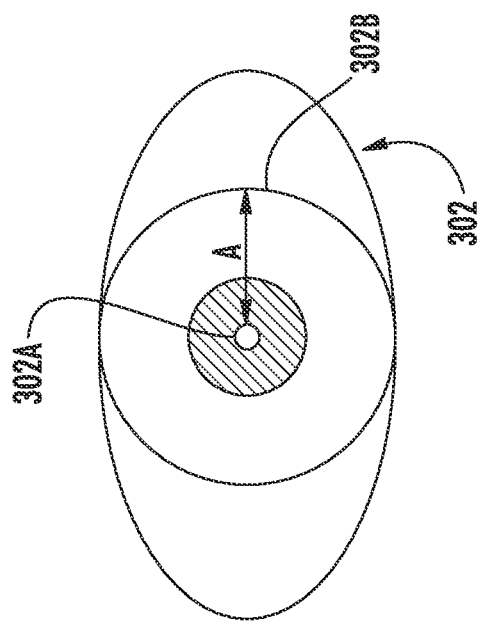
FIG. 3A

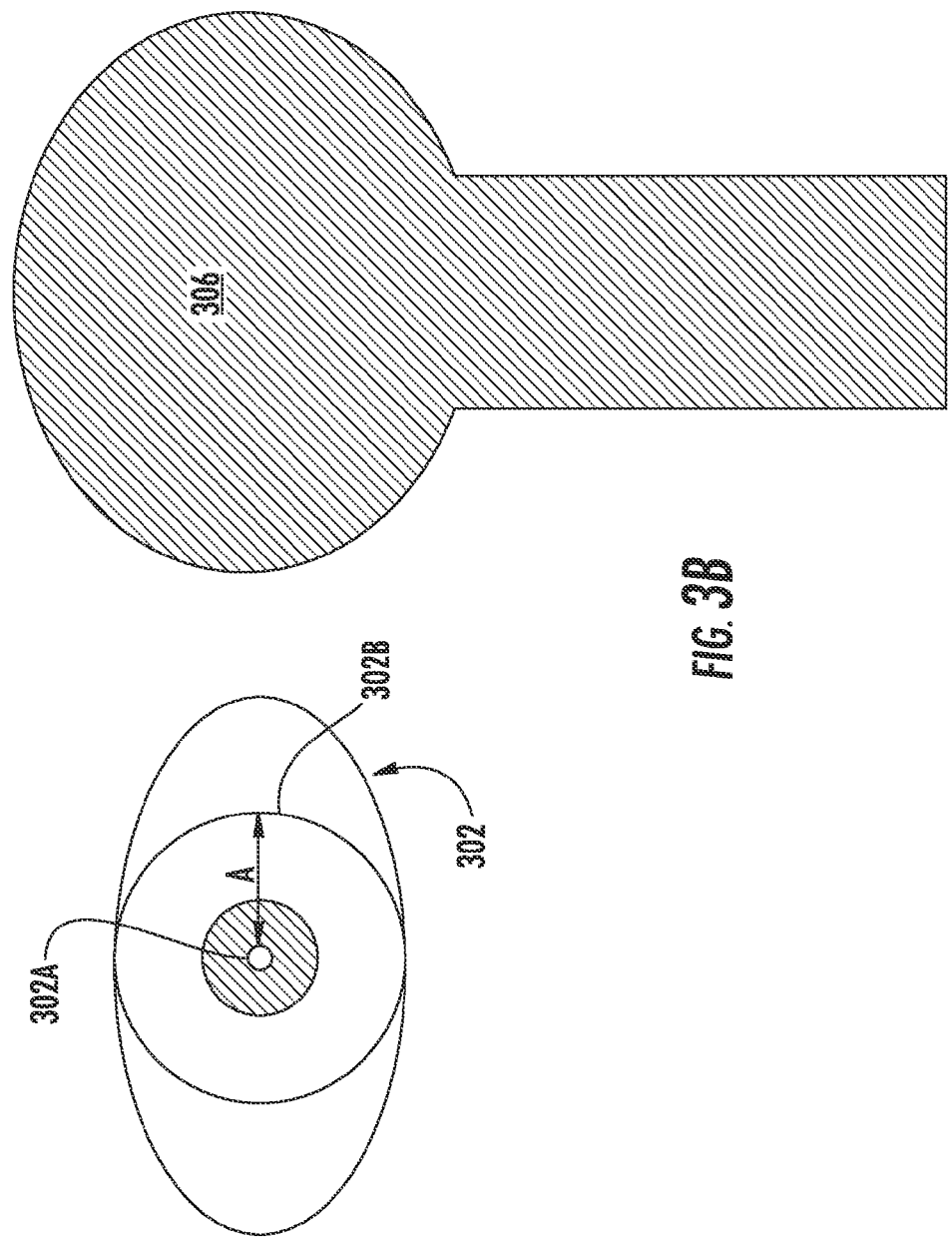

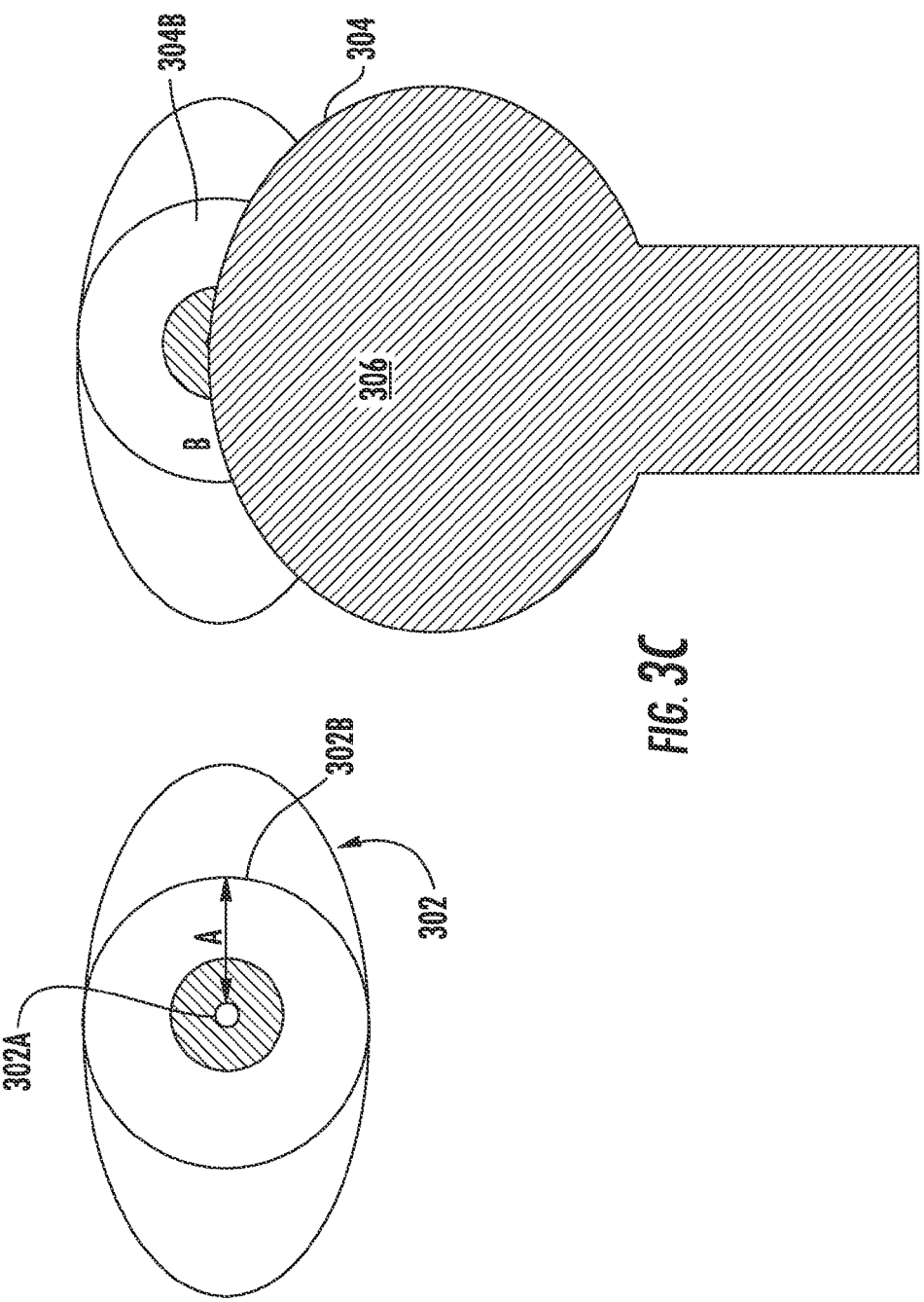

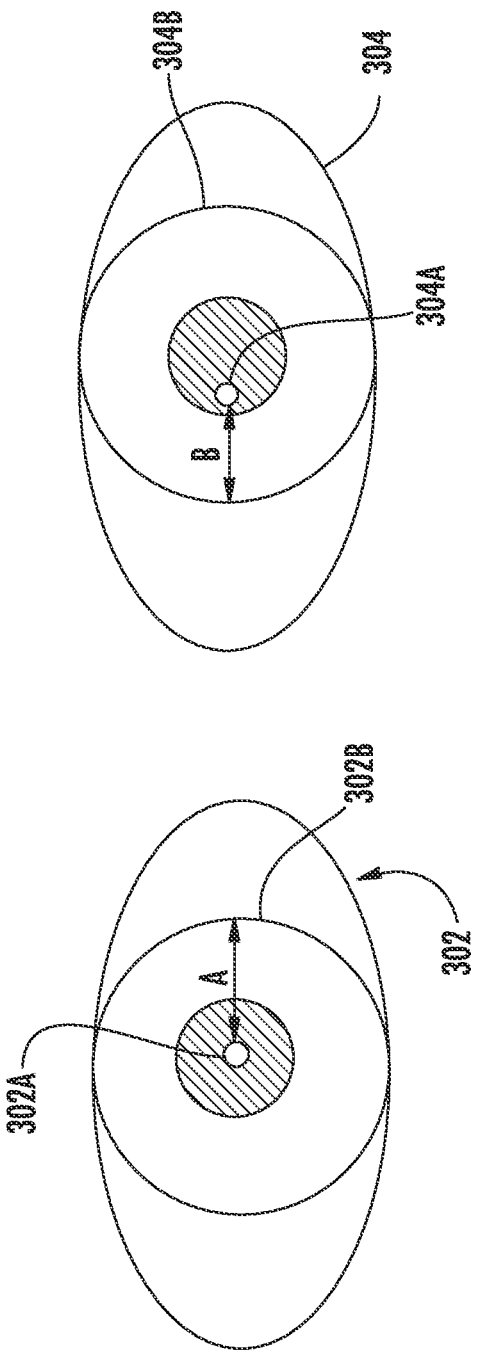

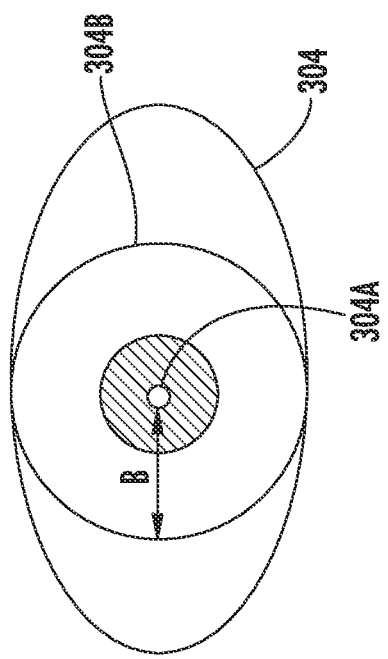
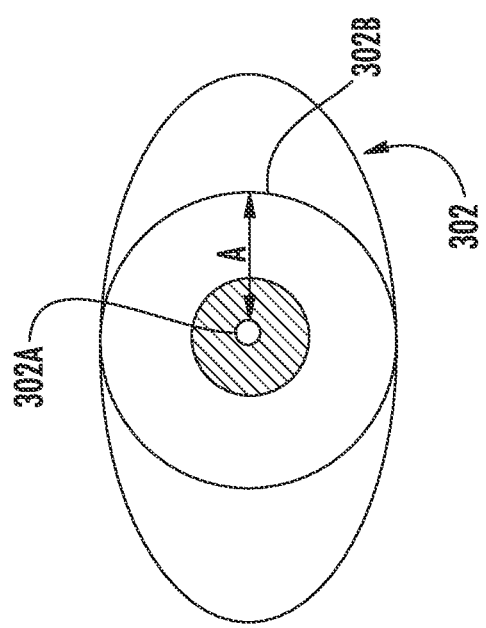
FIG. 3E

Capturing An Image Of At Least One Of The Subject's Eyes Using An Image Capturing Device
402

Analyzing The Image To Identify A Position Of The Reflection Of The Light Within At Least One Of The Subject's Eyes
404

Determining A Phoria Measurement Based On The Position Of The Reflection Of The Light Within At Least One Of The Subject's Eyes
404

FIG. 4

Performing An Autorefraction Measurement, And Capturing An Image Of The Subject's Eyes Using An Image Capturing Device
502

Analyzing The Image To Identify A Position Of The Reflection Of The Light Within Each Of The Subject's Eyes, Respectively, And Determining An Alignment Measurement Of At Least One Of The Subject's Eyes Based On The Position Of The Reflection Of The Light Within Each Of The Subject's Eyes
504

Adjusting The Alignment Measurement Of At Least One Of The Subject's Eyes Based On The Autorefraction Measurement
506

FIG. 5

```
┌─────────────────────────────────────────────────┐
│ PERFORMING AN AUTOREFRACTION MEASUREMENT OF AT LEAST │
│           ONE OF THE SUBJECT'S EYES             │
│                      602                        │
└─────────────────────────────────────────────────┘
                       │
┌─────────────────────────────────────────────────┐
│ PERFORMING AN ALIGNMENT MEASUREMENT OF AT LEAST ONE OF │
│              THE SUBJECT'S EYES                 │
│                      604                        │
└─────────────────────────────────────────────────┘
                       │
┌─────────────────────────────────────────────────┐
│  COMPENSATING THE ALIGNMENT MEASUREMENT BASED ON THE │
│            AUTOREFRACTION MEASUREMENT           │
│                      606                        │
└─────────────────────────────────────────────────┘
```

FIG. 6

```
┌─────────────────────────────────────────────────┐
│ CAPTURING AN IMAGE OF AT LEAST ONE OF THE SUBJECT'S EYES │
│ USING AN IMAGE CAPTURING DEVICE, THE IMAGE INCLUDING AT │
│  LEAST TWO REFLECTIONS OF LIGHT FROM THE SUBJECT'S EYE │
│                      702                        │
└─────────────────────────────────────────────────┘
                       │
┌─────────────────────────────────────────────────┐
│ ANALYZING THE IMAGE TO IDENTIFY RESPECTIVE POSITIONS OF │
│ THE AT LEAST TWO REFLECTIONS OF THE LIGHT WITHIN AT LEAST │
│             ONE OF THE SUBJECT'S EYES           │
│                      704                        │
└─────────────────────────────────────────────────┘
                       │
┌─────────────────────────────────────────────────┐
│    DETERMINING A PHORIA MEASUREMENT BASED ON THE │
│ RESPECTIVE POSITIONS OF THE AT LEAST TWO REFLECTIONS OF │
│  THE LIGHT WITHIN AT LEAST ONE OF THE SUBJECT'S EYES │
│                      706                        │
└─────────────────────────────────────────────────┘
```

FIG. 7

AUTOMATED DETECTION OF EYE ALIGNMENT

CROSS-REFERENCE TO RELATED APPLICATION

This application claims benefit of and priority to U.S. provisional patent application No. 61/901,432, "Automated Detection of Eye Alignment," to Bailey filed on Nov. 7, 2013, which is hereby incorporated by reference in its entirety and made a part hereof.

BACKGROUND

The two main deviations of eye alignment are called tropia and phoria. Tropia (also called strabismus, squint, crossed eyes), is a deviation where the subject cannot point the fovea of both eyes at the same object simultaneously. An exotropia is when one eye constantly points outward, and an esotropia is when one eye constantly points inwards. Similarly, a hypertropia or hypotropia occur when one eye constantly points upwards or downwards. The second type of deviation, phoria, is a latent deviation that is only present when one eye is covered. When both eyes are open, the subject is able to point both eyes at the same object. If an exophoria is present, then the eye that is covered will turn outwards until the cover is removed. Then, it will take up fixation on the same object as the other eye. For an esophoria, the eye that is covered will turn inwards until the cover is removed. For hyperphorias or hypophorias, the eye that is under cover will point upwards or downwards relative to the eye that is not covered. Both tropias and phorias are a source of double vision, discomfort, and can cause difficulty with reading. A tropia can cause permanent vision loss called amblyopia or lazy eye in children. These conditions can be congenital and/or genetic, or acquired through traumatic brain injuries. Both tropia and phoria are established medical conditions that are readily treatable when they are identified. The earlier in life that a tropia is identified, the more likely it is that treatment will reverse/prevent permanent vision loss.

Clinical measurements of tropia and phoria are used across multiple healthcare fields to detect vision problems, either naturally-occurring or due to traumatic brain injury, that would lead to double vision. The predominant, current method for measuring eye alignment, called the cover test, is manual, technically-difficult, and tedious. Other widely-used clinical methods that are automated only determine whether tropia is present, but these methods do not detect the more common deviation in alignment, phoria.

All current methods of measuring eye alignment, either manual or automated, also lack the ability to detect whether or not the subject is accommodating, or focusing the eyes as if to look at an object closer than optical infinity. It is useful for the individual measuring eye alignment to know whether or not someone is accommodating because over- or under-accommodating during a tropia or phoria measurement affects the lateral position of the eye, i.e., how much the eyes are turned inwards or outwards.

Therefore, methods, apparatus and systems are desired that improve the detection and treatment of blinding and debilitating eye alignment disorders and that overcome challenges in the art, some of which are described above.

SUMMARY

Described herein are devices and methods to automate the measurement of the two main deviations of eye alignment.

An example method for automatically measuring a subject's phoria while the subject fixates on a visual target can include capturing an image of at least one of the subject's eyes using an image capturing device. The image can include a reflection of light from at least one of the subject's eyes. The method can also include analyzing the image to identify a position of the reflection of the light within at least one of the subject's eyes, and determining a phoria measurement based on the position of the reflection of the light within at least one of the subject's eyes.

Optionally, the method can include comparing a position of the reflection of the light within one of the subject's eyes (e.g., a left or right eye) and a position of the reflection of the light within another one the subject's eyes (e.g., the right or left eye). The phoria measurement can be determined based on a result of the comparison.

Optionally, the step of analyzing the image to identify a position of the reflection of the light within at least one of the subject's eyes can include identifying a position of the reflection of the light relative to a landmark of at least one of the subject's eyes.

Optionally, the image can include a reflection of the light from at least one of an outer or inner surface of a cornea (e.g., a first or second Purkinje image, respectively) of at least one of the subject's eyes. Alternatively or additionally, the image can include a reflection of the light from at least one of an outer (anterior) or inner (posterior) surface of a lens (e.g., a third or fourth Purkinje image, respectively) of at least one of the subject's eyes. In other words, the image can be a first, second, third or fourth Purkinje image. Although the first through fourth Purkinje images are provided as examples, this disclosure contemplates that the image can include a reflection of the light from any surface of a subject's eye.

Additionally, the method can optionally include sequentially covering and uncovering at least one of the subject's eyes. Additionally, the image can be captured after uncovering at least one of the subject's eyes. Additionally, the method can optionally include capturing a sequence of images of the subject's eyes after uncovering at least one of the subject's eyes and comparing one of the images in the sequence to another of the images in the sequence to determine movement of the eye after the eye is uncovered. Alternatively, the method can optionally include covering at least one of the subject's eyes with a filter, wherein the image is captured while at least one of the subject's eyes is covered by the filter. The filter can be opaque to the subject such that the subject cannot see through the filter, but the filter can pass light of a specified wavelength. Accordingly, the image capturing device can capture the image of at least one of the subject's eyes through the filter.

Optionally, the method can include performing an autorefraction measurement. As used herein, the autorefraction measurement is a measurement a power of a subject's eye by any known technique, including but not limited to, autorefraction or photorefraction. The autorefraction measurement can be taken while the subject is focusing on the visual target, for example. The image can optionally be captured in response to the power of the subject's eye being within a predetermined range. Alternatively or additionally, the method can optionally include adjusting the phoria measurement based on the autorefraction measurement.

Optionally, the method can include calculating an accommodative convergence accommodation ratio based on a position of the reflection of the light within at least one of the subject's eyes and the autorefraction measurement.

As used herein, at least one of the subject's eyes can be the subject's left eye or right eye. Optionally, the phoria measurement can be made based on the subject's left eye or right eye. Alternatively, at least one of the subject's eyes can be the subject's left eye and right eye. Optionally, the phoria measurement can be made based on the subject's left eye and right eye. This disclosure contemplates that the phoria measurement based on the subject's left eye and right eye can be the same or different.

Optionally, the light can be in a visible or non-visible portion of an electromagnetic spectrum. For example, the light can be infrared or visible light. Although infrared and visible light are provided as examples, this disclosure contemplates the light from other portions of the electromagnetic spectrum can be used.

Optionally, the method can include illuminating at least one of the subject's eyes with a light using a light source.

An example apparatus for automatically measuring a subject's phoria while the subject fixates on a visual target can include an image capturing device for capturing an image of at least one of the subject's eyes, a processor, and a memory in operable communication with the processor. The memory can have computer-executable instructions stored thereon that, when executed by the processor, cause the processor to receive the image from the image capturing device, where the image includes a reflection of light from at least one of the subject's eyes, analyze the image to identify a position of the reflection of the light within at least one of the subject's eyes, and determine a phoria measurement based on the position of the reflection of the light within at least one of the subject's eyes.

Optionally, the memory can have further computer-executable instructions stored thereon that, when executed by the processor, cause the processor to compare a position of the reflection of the light within one of the subject's eyes (e.g., a left or right eye) and a position of the reflection of the light within another one the subject's eyes (e.g., the right or left eye). The phoria measurement can be determined based on a result of the comparison.

Optionally, the step of analyzing the image to identify a position of the reflection of the light within at least one of the subject's eyes can include identifying a position of the reflection of the light relative to a landmark of at least one of the subject's eyes.

Optionally, the image can include a reflection of the light from at least one of an outer or inner surface of a cornea (e.g., a first or second Purkinje image, respectively) of at least one of the subject's eyes. Alternatively or additionally, the image can include a reflection of the light from at least one of an outer (anterior) or inner (posterior) surface of a lens (e.g., a third or fourth Purkinje image, respectively) of at least one of the subject's eyes. In other words, the image can be a first, second, third or fourth Purkinje image. Although the first through fourth Purkinje images are provided as examples, this disclosure contemplates that the image can include a reflection of the light from any surface of a subject's eye.

Optionally, the image can be captured after sequentially covering and uncovering at least one of the subject's eyes. Additionally, the image capturing device can be a video capturing device or a camera for capturing a sequence of images of the subject's eyes after uncovering at least one of the subject's eyes and wherein the processor executes computer-readable instructions to compare one of the images in the sequence to another of the images in the sequence to determine movement of the eye after the eye is uncovered. Alternatively, the image can be captured while at least one of the subject's eyes is covered by a filter. The filter can be opaque to the subject such that the subject cannot see through the filter, but the filter can pass light of a specified wavelength. Accordingly, the image capturing device can capture the image of at least one of the subject's eyes through the filter.

Optionally, the apparatus can include a display device. The apparatus can define a first surface and a second surface opposite to the first surface. The display device can be arranged on the first surface, and the image capturing device can be arranged on the second surface. Alternatively or additionally, the apparatus can include a light source for illuminating at least one of the subject's eyes with a light. Optionally, the light source can include one or more light sources. The light source can be any type of light source. For example, the light source can include a plurality of LEDs arranged around a video capturing device. The plurality of LEDs and their arrangement are provided only as an example, and this disclosure contemplates using other numbers, types and/or arrangements for the light source.

Optionally, the apparatus can provide the visual target for the subject. Additionally, the memory can have further computer-executable instructions stored thereon that, when executed by the processor, cause the processor to perform an autorefraction measurement that measures a power of a subject's eye. As used herein, the autorefraction measurement is a measurement the power of a subject's eye by any known technique, including but not limited to, autorefraction or photorefraction. The image can optionally be captured in response to the power of the subject's eye being within a predetermined range. Alternatively or additionally, the memory can have further computer-executable instructions stored thereon that, when executed by the processor, cause the processor to adjust the phoria measurement based on the autorefraction measurement.

Alternatively or additionally, the memory can have further computer-executable instructions stored thereon that, when executed by the processor, cause the processor to calculate an accommodative convergence accommodation ratio based on a position of the reflection of the light within at least one of the subject's eyes and the autorefraction measurement.

Optionally, the apparatus is a computing device. For example, the computing device can optionally be a mobile computing device such as a laptop computer, a tablet computer or a mobile phone.

As described above, at least one of the subject's eyes can be the subject's left eye or right eye. Optionally, the phoria measurement can be made based on the subject's left eye or right eye. Alternatively, at least one of the subject's eyes can be the subject's left eye and right eye. Optionally, the phoria measurement can be made based on the subject's left eye and right eye. This disclosure contemplates that the phoria measurement based on the subject's left eye and right eye can be the same or different.

Optionally, the light can be in a visible or non-visible portion of an electromagnetic spectrum. For example, the light can be infrared or visible light. Although infrared and visible light are provided as examples, this disclosure contemplates the light from other portions of the electromagnetic spectrum can be used.

An example method for automatically measuring alignment of at least one of a subject's eyes can include performing an autorefraction measurement, and capturing an image of the subject's eyes using an image capturing device. As described above, the autorefraction measurement is a measurement a power of a subject's eye by any known technique, including but not limited to, autorefraction or photorefraction. Additionally, the image can include a reflection of light from each of the subject's eyes. The method can also include analyzing the image to identify a position of the reflection of the light within each of the subject's eyes, respectively, and determining an alignment measurement of at least one of the subject's eyes based on the position of the reflection of the light within each of the subject's eyes, respectively.

Optionally, the image is captured in response to the power of at least one of the subject's eyes being within a predetermined range. Alternatively, the method can optionally include adjusting the alignment measurement of at least one of the subject's eyes based on the autorefraction measurement. Additionally, the method can optionally include calculating an accommodative convergence accommodation ratio based on a position of the reflection of the light within at least one of the subject's eyes and the autorefraction measurement.

Additionally, the method can optionally include comparing a position of the reflection of the light within one of the subject's eyes (e.g., a left or right eye) and a position of the reflection of the light within another one the subject's eyes (e.g., the right or left eye). The phoria measurement can be determined based on a result of the comparison.

Optionally, the step of analyzing the image to identify a position of the reflection of the light within each of the subject's eyes, respectively, further comprises identifying a position of the reflection of the light relative to a landmark of each of the subject's eyes, respectively.

Optionally, the image can include a reflection of the light from at least one of an outer or inner surface of a cornea (e.g., a first or second Purkinje image, respectively) of at least one of the subject's eyes. Alternatively or additionally, the image can include a reflection of the light from at least one of an outer (anterior) or inner (posterior) surface of a lens (e.g., a third or fourth Purkinje image, respectively) of at least one of the subject's eyes. In other words, the image can be a first, second, third or fourth Purkinje image. Although the first through fourth Purkinje images are provided as examples, this disclosure contemplates that the image can include a reflection of the light from any surface of a subject's eye.

Optionally, in reference to the method for automatically measuring alignment of at least one of a subject's eyes, the alignment measurement can be a phoria measurement or a tropia measurement.

As described above, at least one of the subject's eyes can be the subject's left eye or right eye. Alternatively, at least one of the subject's eyes can be the subject's left eye and right eye.

Optionally, the light can be in a visible or non-visible portion of an electromagnetic spectrum. For example, the light can be infrared or visible light. Although infrared and visible light are provided as examples, this disclosure contemplates the light from other portions of the electromagnetic spectrum can be used.

Optionally, the method can include illuminating the subject's eyes with a light from a light source.

An apparatus for measuring alignment of at least one of a subject's eyes can include an image capturing device for capturing an image of the subject's eyes, a processor, and a memory in operable communication with the processor. The memory can have computer-executable instructions stored thereon that, when executed by the processor, cause the processor to perform an autorefraction measurement that measures the power of at least one of the subject's eyes while focusing on the visual target, receive the image including a reflection of light from each of the subject's eyes from the image capturing device, analyze the image to identify a position of the reflection of the light within each of the subject's eyes, respectively, and determine an alignment measurement of at least one of the subject's eyes based on the position of the reflection of the light within each of the subject's eyes, respectively.

Optionally, the image is captured in response to the power of at least one of the subject's eyes being within a predetermined range. Alternatively, the memory can have further computer-executable instructions stored thereon that, when executed by the processor, cause the processor to adjust the alignment measurement of at least one of the subject's eyes based on the autorefraction measurement. Additionally, the memory can have further computer-executable instructions stored thereon that, when executed by the processor, cause the processor to calculate an accommodative convergence accommodation ratio based on a position of the reflection of the light within at least one of the subject's eyes and the autorefraction measurement.

Additionally, the memory can have further computer-executable instructions stored thereon that, when executed by the processor, cause the processor to compare a position of the reflection of the light within one of the subject's eyes (e.g., a left or right eye) and a position of the reflection of the light within another one the subject's eyes (e.g., the right or left eye). The phoria measurement can be determined based on a result of the comparison.

Optionally, the step of analyzing the image to identify a position of the reflection of the light within each of the subject's eyes, respectively, further comprises identifying a position of the reflection of the light relative to a landmark of each of the subject's eyes, respectively.

Optionally, the image can include a reflection of the light from at least one of an outer or inner surface of a cornea (e.g., a first or second Purkinje image, respectively) of at least one of the subject's eyes. Alternatively or additionally, the image can include a reflection of the light from at least one of an outer (anterior) or inner (posterior) surface of a lens (e.g., a third or fourth Purkinje image, respectively) of at least one of the subject's eyes. In other words, the image can be a first, second, third or fourth Purkinje image. Although the first through fourth Purkinje images are provided as examples, this disclosure contemplates that the image can include a reflection of the light from any surface of a subject's eye.

Optionally, the apparatus can include a display device. The apparatus can define a first surface and a second surface opposite to the first surface. The display device can be arranged on the first surface, and the image capturing device can be arranged on the second surface. Optionally, the apparatus can include a light source for illuminating the subject's eyes with a light. Alternatively or additionally, the light source can include one or more light sources. The light source can be any type of light source. For example, the light source can include a plurality of LEDs arranged around a video capturing device. The plurality of LEDs and their arrangement are provided only as an example, and this disclosure contemplates using other numbers, types and/or arrangements for the light source.

Optionally, the apparatus is a computing device. For example, the computing device can optionally be a mobile computing device such as a laptop computer, a tablet computer or a mobile phone.

Optionally, in reference to the apparatus for measuring alignment of at least one of a subject's eyes, the alignment measurement can be a phoria measurement or a tropia measurement.

As described above, at least one of the subject's eyes can be the subject's left eye or right eye. Alternatively, at least one of the subject's eyes can be the subject's left eye and right eye.

Optionally, the light can be in a visible or non-visible portion of an electromagnetic spectrum. For example, the light can be infrared or visible light. Although infrared and visible light are provided as examples, this disclosure contemplates the light from other portions of the electromagnetic spectrum can be used.

An example method for measuring alignment of at least one eye can include performing an autorefraction measurement of at least one of a subject's eyes, performing an alignment measurement of at least one of the subject's eyes, and compensating the alignment measurement based on the autorefraction measurement.

As described above, the autorefraction measurement is a measurement a power of a subject's eye by any known technique, including but not limited to, autorefraction or photorefraction. The autorefraction measurement can be taken while the subject is focusing on the visual target, for example. Optionally, the step of compensating the alignment measurement based on the autorefraction measurement includes performing the alignment measurement only when the autorefraction measurement is within a predetermined range. Alternatively, the step of compensating the alignment measurement based on the autorefraction measurement includes adjusting the alignment measurement based on the autorefraction measurement.

Optionally, in reference to the method for measuring alignment of at least one eye, the alignment measurement can be a phoria measurement or a tropia measurement.

An example method for automatically measuring a subject's phoria while the subject fixates on a visual target can include capturing an image of at least one of the subject's eyes using an image capturing device. The image can include at least two reflections of the light from at least one of the subject's eyes. For example, the image can include at least two reflections of the light from at least two of an outer or inner surface of a cornea (e.g., a first or second Purkinje image, respectively) of at least one of the subject's eyes or an outer (anterior) or inner (posterior) surface of a lens (e.g., a third or fourth Purkinje image, respectively) of at least one of the subject's eyes. This disclosure contemplates that the image can include at least two reflections of the light from any two surfaces of a subject's eyes and should not be limited to the above examples (e.g., the first through fourth Purkinje images). The method can also include analyzing the image to identify respective positions of the at least two reflections of the light within at least one of the subject's eyes, and determining a phoria measurement based on the respective positions of the at least two reflections of the light within at least one of the subject's eyes.

Optionally, the method can further include comparing respective positions of the at least two reflections of the light within one of the subject's eyes and respective positions of the at least two reflections of the light within another one the subject's eyes. The phoria measurement can be determined based on a result of the comparison.

Optionally, the method can include illuminating at least one of the subject's eyes with a light using a light source.

An example method for automatically measuring a subject's phoria while the subject fixates on a visual target can include illuminating at least one of the subject's eyes with at least two lights using at least two light sources, and capturing an image of at least one of the subject's eyes using an image capturing device. The image can include reflections of the at least two lights from at least one of the subject's eyes. For example, the image can include reflections of the at least two lights from at least one of an outer or inner surface of a cornea (e.g., a first or second Purkinje image, respectively) of at least one of the subject's eyes or an outer (anterior) or inner (posterior) surface of a lens (e.g., a third or fourth Purkinje image, respectively) of at least one of the subject's eyes. This disclosure contemplates that the image can include reflections of the at least two lights from any surface of a subject's eyes and should not be limited to the above examples (e.g., the first through fourth Purkinje images). The method can also include analyzing the image to identify respective positions of the reflections of the at least two lights within at least one of the subject's eyes, and determining a phoria measurement based on the respective positions of the reflections of the at least two lights within at least one of the subject's eyes.

Optionally, the method can include comparing respective positions of the reflections of the at least two lights within one of the subject's eyes and respective positions of the reflections of the at least two lights within another one the subject's eyes, wherein the phoria measurement is determined based on a result of the comparison.

An example method for automatically measuring a subject's phoria while the subject fixates on a visual target can include capturing an image of at least one of the subject's eyes using an image capturing device. The image can include a landmark within at least one of the subject's eyes. Optionally, the landmark can be a feature within at least one of the subject's eyes such as a blood vessel, for example. This disclosure contemplates that landmarks other than blood vessels can be used. The landmark can be any feature captured and identifiable within the captured image. The method can also include analyzing the image to identify a position of the landmark within at least one of the subject's eyes, and determining a phoria measurement based on the position of the landmark within at least one of the subject's eyes.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIGS. 1A-1C illustrate an example apparatus for performing automated detection of eye alignment according to implementations described herein;

FIGS. 3A-3E illustrate an example automated test for phoria measurement.

FIG. 4 illustrates an example flowchart for a method for automatically measuring a subject's phoria while the subject fixates on a visual target.

FIG. 5 illustrates a flowchart for an example method for automatically measuring alignment of at least one of a subject's eyes.

FIG. 6 illustrates a flowchart of another example method for measuring alignment of at least one eye.

FIG. 7 illustrates a flowchart of another example method for automatically measuring a subject's phoria while the subject fixates on a visual target.

DETAILED DESCRIPTION

Figure 2:
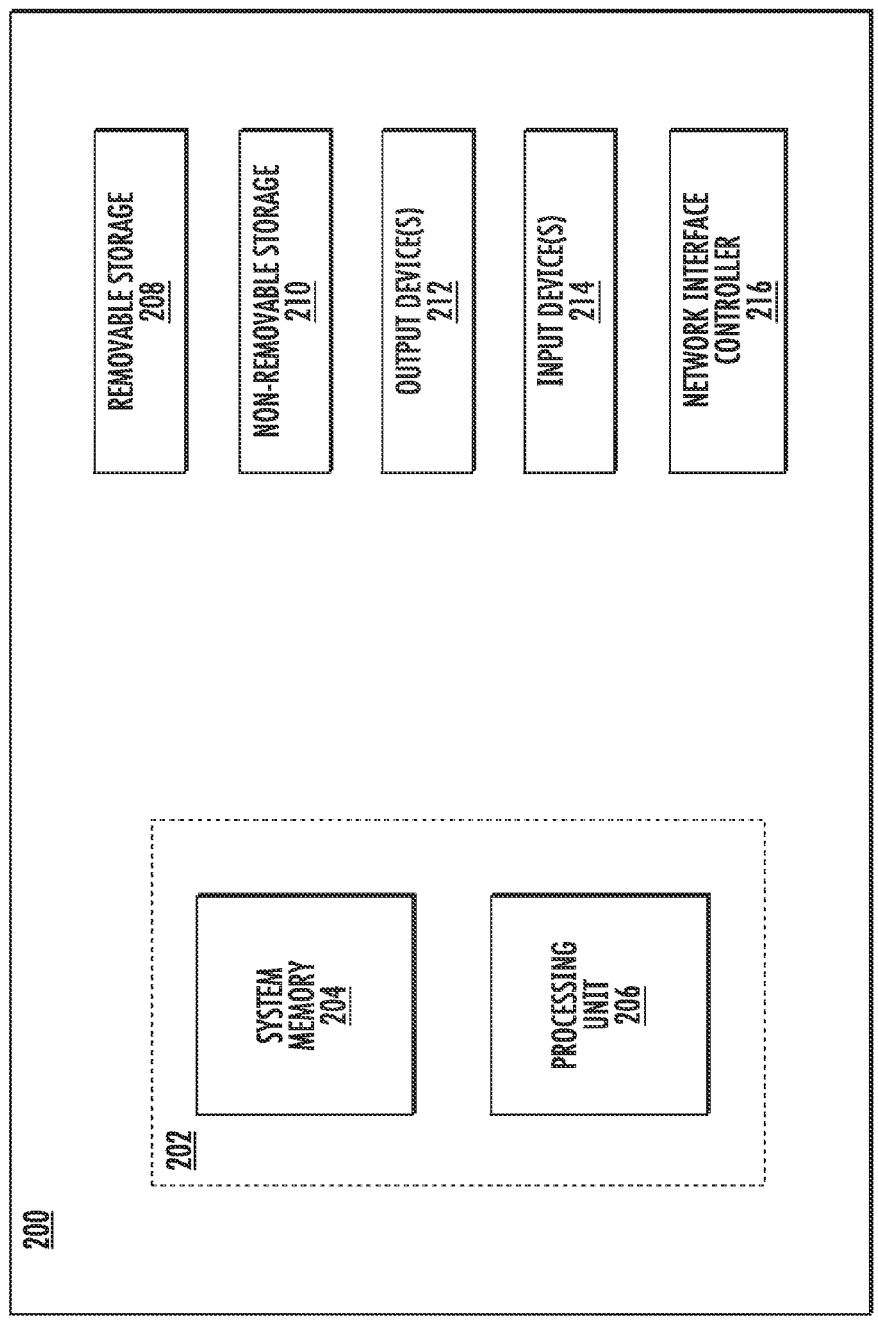
FIG. 2 is a block diagram of an example computing device.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for automated detection of eye lateral alignment, it will become evident to those skilled in the art that the implementations are not limited thereto. For example, the implementations can be used to detect issues with vertical eye alignment and potentially cyclotorsional alignment problems.

Referring now to FIGS. 1A-1C, an example apparatus 100 for performing automated detection of eye alignment is shown. The apparatus 100 can be used to perform any of the automated techniques for measuring phoria and/or tropia described in detail below. FIG. 1A illustrates a first surface (e.g., a front surface) 100A of the apparatus 100. FIG. 1B illustrates a second surface (e.g., a back surface) 100B that is opposite to the first surface 100A. Optionally, the apparatus 100 can include a light source 120 for illuminating one or more of the subject's eyes with a light, an image capturing device 110, such as a camera, for capturing an image of one or more of the subject's eyes, a processor, and a memory in operable communication with the processor. Although the processor and the memory are not shown in FIGS. 1A-1C, the processor and memory are described in detail with regard to FIG. 2 below. Optionally, the image capturing device 110 can be a video capturing device. The apparatus 100 can also include a display device 130. As shown in FIGS. 1A-1C, the display device 130 can be arranged on the first surface 100A, and the image capturing device 120 and the light source 110 can be arranged on the second surface 100B.

Optionally, the apparatus 100 can include a case 180 for housing a mobile computing device such as a tablet computer or a mobile phone, for example. The mobile computing device can include one or more input/output devices. For example, the mobile computing device can optionally include touch-sensitive display device. The touch-sensitive display device can be accessible/visible through the case. Alternatively or additionally, the mobile computing device can optionally include one or more switches, knobs or other controls that are accessible/visible through the case. The apparatus 100 can have an ergonomic design. Additionally, the apparatus 100 can be provided with visual markings. For example, as shown in FIG. 1A, the apparatus 100 can be provided with a visual locator 140 on the first surface 100A that aligns with the image capturing device 110 arranged on the second surface 100B. Alternatively or additionally, as shown in FIG. 1B, the apparatus 100 can be provided with a visual locator 150 on the second surface 100B to provide a visual target to the subject. Optionally, the visual locator 150 can be "cross-hairs" (or another marking) arranged near the image capturing device 110 on which the subject fixates during the alignment tests. Optionally, as shown in FIG. 1B, the apparatus 100 can be provided with one or more raised portions 160 on the second surface 100B to facilitate picking up the apparatus 100 from a flat surface.

The optional light source 120 can include one or more light sources. This disclosure contemplates that the light source 120 can be any type of light source. For example, as shown in FIG. 1B, the light source 120 can be integrated into the case that comprises that apparatus 100 and include a plurality of LEDs arranged around the image capturing device 110 (e.g., 12 LEDs arranged in a ring). The plurality of LEDs and their arrangement shown in FIG. 1B are provided only as an example, and this disclosure contemplates using other numbers, types and/or arrangements for the light source 120. Alternatively, in embodiments of the invention no additional light source is provided and the apparatus 100 utilizes ambient or available light. Alternatively, a separate light source such as a lamp, flashlight and the like can be used to practice embodiments of the invention.

FIG. 1C is a side profile view of the apparatus 100 for performing automated detection of eye alignment. While FIGS. 1A-1C generally illustrate a mobile computing device such as a tablet computer or a mobile phone, for example, incorporated into a case 180 for performing automated detection of eye alignment, the invention is not to be limited to this embodiment. The apparatus can be stand alone comprising at least an image capturing device for capturing an image of at least one of the subject's eyes; a processor; and a memory in operable communication with the processor. In other embodiments, the apparatus can utilize or be incorporated into devices such as Google Glass (Google Corporation, Mountain View, Calif. USA), watches, other vision testing apparatus and devices, and the like.

When the logical operations described herein are implemented in software, the process may execute on any type of computing architecture or platform. For example, referring to FIG. 2, an example computing device upon which embodiments of the invention may be implemented is illustrated. The computing device 200 can optionally be a mobile computing device such as a laptop computer, a tablet computer or a mobile phone. The computing device 200 may include a bus or other communication mechanism for communicating information among various components of the computing device 200. In its most basic configuration, computing device 200 typically includes at least one processing unit 206 and system memory 204. Depending on the exact configuration and type of computing device, system memory 204 may be volatile (such as random access memory (RAM)), non-volatile (such as read-only memory (ROM), flash memory, etc.), or some combination of the two. This most basic configuration is illustrated in FIG. 2 by dashed line 202. The processing unit 206 may be a standard programmable processor that performs arithmetic and logic operations necessary for operation of the computing device 200.

Computing device 200 may have additional features/functionality. For example, computing device 200 may include additional storage such as removable storage 208 and non-removable storage 210 including, but not limited to, magnetic or optical disks or tapes. Computing device 200 may also contain network connection(s) 216 that allow the device to communicate with other devices. Computing device 200 may also have input device(s) 214 such as a keyboard, mouse, touch screen, etc. Output device(s) 212 such as a display, speakers, printer, etc. may also be included. The additional devices may be connected to the bus in order to facilitate communication of data among the components of the computing device 200. All these devices are well known in the art and need not be discussed at length here.

The processing unit 206 may be configured to execute program code encoded in tangible, computer-readable media. Computer-readable media refers to any media that is capable of providing data that causes the computing device 200 (i.e., a machine) to operate in a particular fashion. Various computer-readable media may be utilized to provide instructions to the processing unit 206 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 206 may execute program code stored in the system memory 204. For example, the bus may carry data to the system memory 204, from which the processing unit 206 receives and executes instructions. The data received by the system memory 204 may optionally be stored on the removable storage 208 or the non-removable storage 210 before or after execution by the processing unit 206.

Computing device 200 typically includes a variety of computer-readable media. Computer-readable media can be any available media that can be accessed by device 200 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 204, removable storage 208, and non-removable storage 210 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 200. Any such computer storage media may be part of computing device 200.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

The techniques for automated eye alignment measurement described herein can optionally be implemented with a mobile computing device, such as a laptop computer, tablet computer or mobile phone. Accordingly, the mobile computing device is extremely small compared to conventional devices and is very portable, which allows the mobile computing device to be used when testing for eye alignment needs to be conducted in multiple gazes. This is important for optometry, ophthalmology, neurology, and emergency medicine because testing the integrity of the cranial nerves depends on the multiple gaze aspect of this testing. Many conventional devices have a chin rest that requires the subjects to only look straight ahead during this testing. Unlike conventional devices, the mobile computing device can be placed in any position relative to the subject's head where the eyes can still be viewed and measurements can be made. This would also be true for a traumatic brain injury subject who is supine, where cranial nerve testing would be challenging for the clinician to perform.

As described above, phoria is a latent deviation that is only present when one eye is covered. When both eyes are open and uncovered the subject is able to point both eyes at the same object. Using the automated phoria measurement tests described below, it is possible to eliminate the need for the prismatic estimation of the magnitude and direction of the tropia or phoria measurement that is typically used in the manual measurement method, cover test. Instead, a computing device with an image capturing device and a light source (e.g., the apparatus shown in FIGS. 1A-1B) can be used. In an example implementation (FIGS. 3A-3E), the automated phoria measurement test can use the Purkinje I Image (i.e., a reflection of light of the outer surface of the cornea). The clinician can cover one the subject's eyes as usual and remove the cover while the image capturing device (e.g., a camera, a video camera, etc.) is recording the covered eye and the Purkinje Image I for the uncovered eye. After the cover is removed, the image capturing device records the Purkinje I image for both eyes. For example, the image capturing device can record a series of still images or a continuous video. It takes approximately 1 to 2 seconds for the uncovered eye to look at an object again once the cover is removed. Thus, the images that are captured during those 1 to 2 seconds are analyzed. The actual measurement is accomplished by looking at the location of the Purkinje I images relative to where they are located within the visible portion of the iris in both eyes. From these relative positions, it is possible to determine where the eye was pointing under cover, i.e., a phoria measurement, in a manner that is similar to the Hirshberg Test for tropia.

Optionally, automated tropia and phoria measurements can be performed with measurements of the power of the eye obtained with autorefraction. If a subject is looking very far away, the power of the eye that is measured with autorefraction is an estimate of the subject's glasses prescription. If, however, the subject is looking at a near target, an autorefractor can measure how much the subject is focusing to see that near object. The tropia and phoria measurements are always done both while the subject is looking at distance and also while the subject is looking at a near target. It is important that during the distance measurement the eyes are completely relaxed, and that during the near measurement the eyes are focusing accurately. The near tropia and phoria measurements will be different from the distance tropia and phoria measurements only if a subject has an abnormal accommodative convergence accommodation (AC/A) ratio. The AC/A ratio is the amount that they eye turns inwards (e.g., accommodative convergence, AC) for each unit of power for focusing on a near-target (e.g., accommodation, A). Accommodation and accommodative convergence are neurologically linked. If someone with an abnormal AC/A under or over focuses on a near target, the clinician will get a different near phoria or tropia measurement than if the subject is focusing accurately. AC/A can be calculated by having someone look at two or more different targets that require different amounts of accommodation (two different denominators, "A") and comparing the accommodative convergence (the numerator, "AC") and calculating the difference between the convergence for the one target and the other target to determine the AC/A. According to the techniques described here, the same camera and light can be used to perform simultaneous tropia/phoria and autorefraction measurements. This allows the clinician to only make the measurement when the subject is accommodating at a certain level, or to adjust the tropia/phoria measurement based on the accommodative effort that was exerted, thus improving the accuracy of the measurement.

In addition, all of these same imaging measurements provide a measurement of each subject's AC/A. Thus, it is possible to determine how much the eye turned inward (e.g., accommodative convergence, AC) from the position of the Purkinje I image for both eyes and how much the subject accommodated (A). Currently, there are no automated measurements of AC/A. Currently, the cover test is performed at multiple distances that require different levels of accommodation, and the ratio is determined from at least two such measurements, or lenses are placed in front of the eye and the clinician assumes that the subject accommodates the same amount as the lenses. A phoria measurement is done with and without the lenses to determine the accommodative convergence (AC).

Referring now to FIGS. 3A-3E an example automated test for phoria measurement is shown. In FIG. 3A, the subject's right and left eyes are fixated at the same place. The subject's eyes (e.g., at least one of the subject's eyes) can be illuminated with a light using a light source. Optionally, ambient or available light can be used, wherein no additional light source is required. Optionally, the light can be in a visible or non-visible portion of an electromagnetic spectrum. For example, the light can be infrared or visible light. Although infrared and visible light are provided as examples, this disclosure contemplates the light from other portions of the electromagnetic spectrum can be used.

An image of the subject's eyes can be captured using an image capturing device, for example. As shown in FIG. 3A, the image can include a reflection of the light from the subject's eyes or another landmark feature (blood vessel, visible portion of the iris, iris feature, center of the pupil, center of the visible iris diameter, etc.). For example, a reflection of the light 302A from the subject's right eye 302 and a reflection of light 304A from the subject's left eye 304 are shown. Optionally, the image can include a reflection of the light from at least one of an outer or inner surface of a cornea (e.g., a first or second Purkinje image, respectively) of the subject's eyes. Alternatively or additionally, the image can include a reflection of the light from at least one of an outer (anterior) or inner (posterior) surface of a lens (e.g., a third or fourth Purkinje image, respectively) of the subject's eyes. In other words, the image can be a first, second, third or fourth Purkinje image. Although the first through fourth Purkinje images are provided as examples, this disclosure contemplates that the image can include a reflection of the light from any surface of a subject's eye. Further, this disclosure contemplates that any other feature of the eye (blood vessel, visible portion of the iris, iris feature, center of the pupil, center of the visible iris diameter, etc.) can be used to track its position or movement, thus not requiring a reflection.

In FIG. 3A, distance "A" is the distance between the reflection of the light 302A from the subject's right eye 302 and a visible portion of an iris 302B of the subject's right eye 302, and distance "B" is the distance between the reflection of light 304A from the subject's left eye 304 and a visible portion of an iris 304B of the subject's left eye 304. Because distance "A" equals distance "B," no tropia is present. To determine if a phoria is present, one of the subject's eyes can be sequentially covered and uncovered. Optionally, a sequence of images can be captured after uncovering one of the subject's eyes. As described below, the reflection of the light within at least one of the subject's eyes in one of the sequence of images can be compared to a position of the reflection of the light within the at least one of the subject's eyes in another of the sequence of images to determine any movement after the subject's eye is uncovered and phoria or tropia magnitude and direction can be calculated from the movement.

In FIG. 3B, the subject's left eye 304 is covered with a cover 306. In FIG. 3C, the subject's left eye 304 is partially uncovered. As described above, images can be captured with sequentially covering and uncovering the subject's left eye 304. In FIG. 3D, the subject's left eye 304 is completely uncovered. Similar to above, an image of the subject's eyes can be captured using the image capturing device when the subject's left eye 304 is completely uncovered. As shown in FIG. 3D, the image can include a reflection of the light from the subject's eyes, e.g., a reflection of the light 302A from the subject's right eye 302 and a reflection of light 304A from the subject's left eye 304 are shown. In FIG. 3D, distance "A" is the distance between the reflection of the light 302A from the subject's right eye 302 and a visible portion of an iris 302B of the subject's right eye 302, and distance "B" is the distance between the reflection of light 304A from the subject's left eye 304 and a visible portion of an iris 304B of the subject's left eye 304. Because distance "A" is not equal to distance "B," a phoria is present. For example, in FIG. 3D because distance "B" is less than distance "A," an exophoria is present. The phoria measurement can be determined based on the position of the reflection of the light within the subject's eyes in FIG. 3D.

After approximately 1-2 seconds, the subject's left eye 304 (e.g., the eye that was sequentially covered and uncovered), takes up fixation again on the same place as the subject's right eye 302. Thus, as shown in FIG. 3E, distance "A" is the distance between the reflection of the light 302A from the subject's right eye 302 and a visible portion of an iris 302B of the subject's right eye 302, and distance "B" is the distance between the reflection of light 304A from the subject's left eye 304 and a visible portion of an iris 304B of the subject's left eye 304. Because distance "A" equals to distance "B," no a tropia is present.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

FIG. 4 illustrates an example method for automatically measuring a subject's phoria while the subject fixates on a visual target. This embodiment of a method can include Step 402, capturing an image of at least one of the subject's eyes using an image capturing device. The image can include a reflection of the light from at least one of the subject's eyes. The method can also include Step 404, analyzing the image to identify a position of the reflection of the light within at least one of the subject's eyes, and Step 406, determining a phoria measurement based on the position of the reflection of the light within at least one of the subject's eyes.

Optionally, the method can include comparing a position of the reflection of the light within one of the subject's eyes (e.g., a left or right eye) and a position of the reflection of the light within another one the subject's eyes (e.g., the right or left eye). The phoria measurement can be determined based on a result of the comparison.

Optionally, the step of analyzing the image to identify a position of the reflection of the light within at least one of the subject's eyes can include identifying a position of the reflection of the light relative to a landmark of at least one of the subject's eyes.

Optionally, the image can include a reflection of the light from at least one of an outer or inner surface of a cornea (e.g., a first or second Purkinje image, respectively) of at least one of the subject's eyes. Alternatively or additionally, the image can include a reflection of the light from at least one of an outer (anterior) or inner (posterior) surface of a lens (e.g., a third or fourth Purkinje image, respectively) of at least one of the subject's eyes. In other words, the image can be a first, second, third or fourth Purkinje image. Although the first through fourth Purkinje images are provided as examples, this disclosure contemplates that the image can include a reflection of the light from any surface of a subject's eye.

Additionally, the method can optionally include sequentially covering and uncovering at least one of the subject's eyes. Additionally, the image can be captured after uncovering at least one of the subject's eyes. Additionally, the method can optionally include capturing a sequence of images of the subject's eyes after uncovering at least one of the subject's eyes and comparing the reflection of the light within at least one of the subject's eyes in one of the sequence of images to a position of the reflection of the light within the at least one of the subject's eyes in another of the sequence of images to determine any movement after the subject's eye is uncovered.

Alternatively, the method can include covering at least one of the subject's eyes with a filter, wherein the image is captured while at least one of the subject's eyes is covered by the filter. The filter can be opaque to the subject such that the subject cannot see through the filter, but the filter can pass light of a specified wavelength (e.g., infrared light). An example filter is the WRATTEN #89B from EASTMAN KODAK COMPANY of ROCHESTER, N.Y. It should be understood that the WRATTEN #89B is provided only as an example and that other filters can be used, including filters that pass light with wavelengths other than infrared. Accordingly, the image capturing device can capture the image of at least one of the subject's eyes through the filter. In other words, the alignment measurement can be performed without sequentially covering and uncovering at least one of the subject's eyes.

Optionally, the method can include performing an autorefraction measurement. As used herein, the autorefraction measurement is a measurement a power of a subject's eye by any known technique, including but not limited to, autorefraction or photorefraction. The autorefraction measurement can be taken while the subject is focusing on the visual target, for example. The image can optionally be captured in response to the power of the subject's eye being within a predetermined range. Alternatively or additionally, the method can optionally include adjusting the phoria measurement based on the autorefraction measurement.

Optionally, the method can include calculating an accommodative convergence accommodation ratio based on a position of the reflection of the light within at least one of the subject's eyes and the autorefraction measurement.

FIG. 5 illustrates a flowchart for an example method for automatically measuring alignment of at least one of a subject's eyes. This embodiment of a method can include Step 502, performing an autorefraction measurement, and capturing an image of the subject's eyes using an image capturing device. As described above, the autorefraction measurement is a measurement a power of a subject's eye by any known technique, including but not limited to, autorefraction or photorefraction. Additionally, the image can include a reflection of the light from each of the subject's eyes. The method can also include Step 504, analyzing the image to identify a position of the reflection of the light within each of the subject's eyes, respectively, and determining an alignment measurement of at least one of the subject's eyes based on the position of the reflection of the light within each of the subject's eyes, respectively.

Optionally, the image is captured in response to the power of at least one of the subject's eyes being within a predetermined range. Alternatively, the method can optionally include Step 506, adjusting the alignment measurement of at least one of the subject's eyes based on the autorefraction measurement. Additionally, the method can optionally include calculating an accommodative convergence accommodation ratio based on a position of the reflection of the light within at least one of the subject's eyes and the autorefraction measurement.

Additionally, the method can optionally include comparing a position of the reflection of the light within one of the subject's eyes (e.g., a left or right eye) and a position of the reflection of the light within another one the subject's eyes (e.g., the right or left eye). The phoria measurement can be determined based on a result of the comparison.

Optionally, the step of analyzing the image to identify a position of the reflection of the light within each of the subject's eyes, respectively, further comprises identifying a position of the reflection of the light relative to a landmark of each of the subject's eyes, respectively.

Optionally, the image can include a reflection of the light from at least one of an outer or inner surface of a cornea (e.g., a first or second Purkinje image, respectively) of at least one of the subject's eyes. Alternatively or additionally, the image can include a reflection of the light from at least one of an outer (anterior) or inner (posterior) surface of a lens (e.g., a third or fourth Purkinje image, respectively) of at least one of the subject's eyes. In other words, the image can be a first, second, third or fourth Purkinje image. Although the first through fourth Purkinje images are provided as examples, this disclosure contemplates that the image can include a reflection of the light from any surface of a subject's eye.

Optionally, the alignment measurement can be a phoria measurement or a tropia measurement.

FIG. 6 illustrates a flowchart of another example method for measuring alignment of at least one eye. This embodiment of a method can include Step 602, performing an autorefraction measurement of at least one of a subject's eyes, Step 604, performing an alignment measurement of at least one of the subject's eyes, and Step 606, compensating the alignment measurement based on the autorefraction measurement.

As described above, the autorefraction measurement is a measurement of the power of a subject's eye by any known technique, including but not limited to, autorefraction or photorefraction. The autorefraction measurement can be taken while the subject is focusing on the visual target, for example. Optionally, the step of compensating the alignment measurement based on the autorefraction measurement includes performing the alignment measurement only when the autorefraction measurement is within a predetermined range. Alternatively, the step of compensating the alignment measurement based on the autorefraction measurement includes adjusting the alignment measurement based on the autorefraction measurement.

Optionally, the alignment measurement can be a phoria measurement or a tropia measurement.

FIG. 7 illustrates a flowchart of another example method for automatically measuring a subject's phoria while the subject fixates on a visual target. This embodiment of a method can include Step 702, capturing an image of at least one of the subject's eyes using an image capturing device. The image can include at least two reflections of the light from at least one of the subject's eyes. For example, the image can include at least two reflections of the light from at least two of an outer or inner surface of a cornea (e.g., a first or second Purkinje image, respectively) of at least one of the subject's eyes or an outer (anterior) or inner (posterior) surface of a lens (e.g., a third or fourth Purkinje image, respectively) of at least one of the subject's eyes. This disclosure contemplates that the image can include at least two reflections of the light from any two surfaces of a subject's eyes and should not be limited to the above examples (e.g., the first through fourth Purkinje images). The method can also include Step 704, analyzing the image to identify respective positions of the at least two reflections of the light within at least one of the subject's eyes, and determining a phoria measurement based on the respective positions of the at least two reflections of the light within at least one of the subject's eyes.

Optionally, the method can further include comparing respective positions of the at least two reflections of the light within one of the subject's eyes and respective positions of the at least two reflections of the light within another one the subject's eyes. The phoria measurement can be determined based on a result of the comparison.

Figure 8:
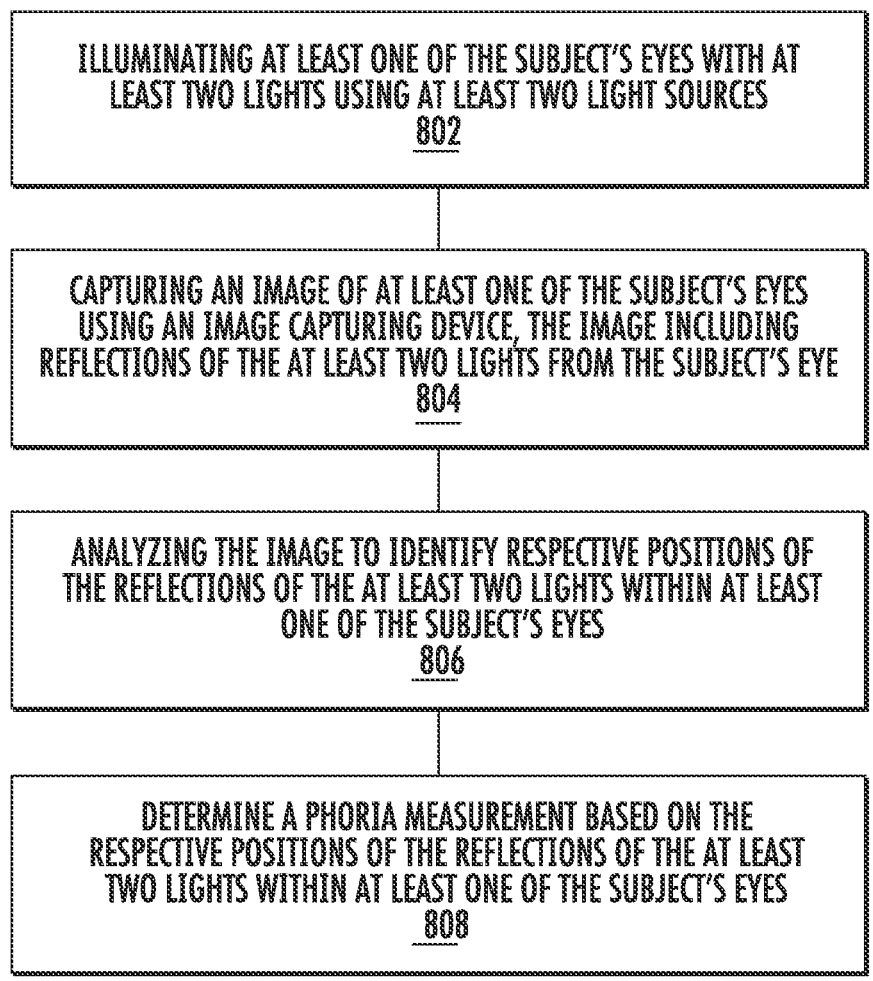
FIG. 8 illustrates a flowchart of yet another example method for automatically measuring a subject's phoria while the subject fixates on a visual target.

FIG. 8 illustrates a flowchart of yet another example method for automatically measuring a subject's phoria while the subject fixates on a visual target. This embodiment of a method can include Step 802, illuminating at least one of the subject's eyes with at least two lights using at least two light sources, and Step 804, capturing an image of at least one of the subject's eyes using an image capturing device. The image can include reflections of the at least two lights from at least one of the subject's eyes. For example, the image can include reflections of the at least two lights from at least one of an outer or inner surface of a cornea (e.g., a first or second Purkinje image, respectively) of at least one of the subject's eyes or an outer (anterior) or inner (posterior) surface of a lens (e.g., a third or fourth Purkinje image, respectively) of at least one of the subject's eyes. This disclosure contemplates that the image can include reflections of the at least two lights from any surface of a subject's eyes and should not be limited to the above examples (e.g., the first through fourth Purkinje images). The method can also include Step 806, analyzing the image to identify respective positions of the reflections of the at least two lights within at least one of the subject's eyes, and Step 808, determining a phoria measurement based on the respective positions of the reflections of the at least two lights within at least one of the subject's eyes.

Optionally, the method can include comparing respective positions of the reflections of the at least two lights within one of the subject's eyes and respective positions of the reflections of the at least two lights within another one the subject's eyes, wherein the phoria measurement is determined based on a result of the comparison.

Figure 9:
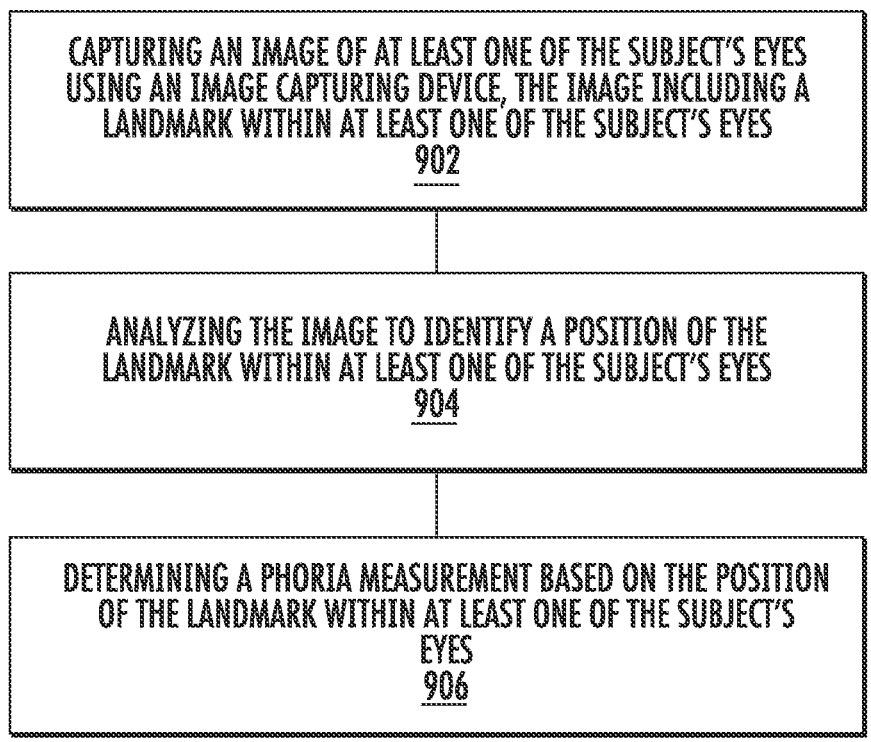
FIG. 9 illustrates a flowchart of another example method for automatically measuring a subject's phoria while the subject fixates on a visual target.

FIG. 9 illustrates a flowchart of another example method for automatically measuring a subject's phoria while the subject fixates on a visual target. This embodiment of a method can include Step 902, capturing an image of at least one of the subject's eyes using an image capturing device. The image can include a landmark within at least one of the subject's eyes. Optionally, the landmark can be a feature within at least one of the subject's eyes such as a blood vessel, for example. This disclosure contemplates that landmarks other than blood vessels can be used such as a feature of the iris, the visible portion of the iris, the midpoint of the pupil, or the midpoint of the visible iris, and the like. The landmark can be any feature captured and identifiable within the captured image. The method can also include Step 904, analyzing the image to identify a position of the landmark within at least one of the subject's eyes, and Step 906, determining a phoria measurement based on the position of the landmark within at least one of the subject's eyes.

As used herein, at least one of the subject's eyes can be the subject's left eye or right eye. Optionally, the phoria measurement can be made based on the subject's left eye or right eye. Alternatively, at least one of the subject's eyes can be the subject's left eye and right eye. Optionally, the phoria measurement can be made based on the subject's left eye and right eye. This disclosure contemplates that the phoria measurement based on the subject's left eye and right eye can be the same or different.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for automatically measuring a subject's phoria while the subject fixates on a visual target, comprising:
    capturing an image of at least one of the subject's eyes using an image capturing device, the image including a reflection of light from any surface of the at least one of the subject's eyes;
    analyzing the image to identify a position of the reflection of the light within the at least one of the subject's eyes;
    determining a phoria measurement based on the position of the reflection of the light within the at least one of the subject's eyes;
    performing an autorefraction measurement, the autorefraction measurement measuring a power of one of the subject's eyes while focusing on the visual target; and
    calculating an accommodative convergence accommodation ratio based on a position of the reflection of the light within at least one of the subject's eyes and the autorefraction measurement.

2. The method of claim 1, further comprising comparing a position of the reflection of the light within one of the subject's eyes and a position of the reflection of the light within another one of the subject's eyes, wherein the phoria measurement is determined based on a result of the comparison.

3. The method of claim 1, wherein analyzing the image to identify a position of the reflection of the light within the at least one of the subject's eyes further comprises identifying a position of the reflection of the light relative to a landmark of the at least one of the subject's eyes.

4. The method of claim 1, wherein the image includes a reflection of the light from at least one of an outer or inner surface of a cornea or an outer or inner surface of a lens of the at least one of the subject's eyes.

5. The method of claim 4, wherein the image is a first, second, third or fourth Purkinje image.

6. The method of claim 1, further comprising covering and uncovering the at least one of the subject's eyes, wherein the image is captured after uncovering the at least one of the subject's eyes.

7. The method of claim 6, further comprising capturing a sequence of images of the subject's eyes after uncovering the at least one of the subject's eyes, and comparing a position of the reflection of the light within the at least one of the subject's eyes in one of the sequence of images to a position of the reflection of the light within the at least one of the subject's eyes in another of the sequence of images to determine any a magnitude and a direction of any movement after the at least one of the subject's eyes is uncovered.

8. The method of claim 1, further comprising covering at least one of the subject's eyes with a filter, wherein the image is captured while at least one of the subject's eyes is covered by the filter.

9. The method of claim 1, wherein the image is captured in response to the power of the one of the subject's eyes being within a predetermined range.

10. The method of claim 1, further comprising adjusting the phoria measurement based on the autorefraction measurement.

11. The method of claim 1, further comprising illuminating at least one of the subject's eyes with a light using a light source to create the reflection, wherein the light is in a visible or non-visible portion of an electromagnetic spectrum.

12. An apparatus for automatically measuring a subject's phoria while the subject fixates on a visual target, comprising:
    an image capturing device for capturing an image of at least one of the subject's eyes;
    a processor; and
    a memory in operable communication with the processor, the memory having computer-executable instructions stored thereon that, when executed by the processor, cause the processor to:
        receive the image from the image capturing device, the image including a reflection of light from any surface of the at least one of the subject's eyes;
        analyze the image to identify a position of the reflection of the light within the at least one of the subject's eyes;
        determine a phoria measurement based on the position of the reflection of the light within the at least one of the subject's eyes;
        perform an autorefraction measurement that measures a power of the one of the subject's eyes while focusing on the visual target; and
        calculate an accommodative convergence accommodation ratio based on a position of the reflection of the light within at least one of the subject's eyes and the autorefraction measurement.

13. The apparatus of claim 12, wherein the memory has further computer-executable instructions stored thereon that, when executed by the processor, cause the processor to compare a position of the reflection of the light within one of the subject's eyes and a position of the reflection of the light within another one the subject's eyes, wherein the phoria measurement is determined based on a result of the comparison.

14. The apparatus of claim 12, wherein analyzing the image to identify a position of the reflection of the light within at least one of the subject's eyes further comprises identifying a position of the reflection of the light relative to a landmark of the at least one of the subject's eyes.

15. The apparatus of claim 12, wherein the image includes a reflection of the light from at least one of an outer or inner surface of a cornea or an outer or inner surface of a lens of at least one of the subject's eyes.

16. The apparatus of claim 15, wherein the image is a first, second, third or fourth Purkinje image.

17. The apparatus of claim 12, wherein the image is captured after covering and uncovering the at least one of the subject's eyes.

18. The apparatus of claim 17, wherein the image capturing device is a video capturing device or a camera for capturing a sequence of images of the subject's eyes after uncovering the at least one of the subject's eyes and wherein the processor executes computer readable instructions to compare a position of the reflection of the light within the at least one of the subject's eyes in one of the sequence of images to a position of the reflection of the light within the at least one of the subject's eyes in another of the sequence of images to determine a magnitude and a direction any movement after the at least one of the subject's eyes is uncovered.

19. The apparatus of claim 18, further comprising a display device, wherein the apparatus defines a first surface and a second surface opposite to the first surface, the display device being arranged on the first surface and the image capturing device being arranged on the second surface.

20. The apparatus of claim 12, wherein the image is captured while at least one of the subject's eyes is covered by a filter.

21. The apparatus of claim 12, further comprising a light source for illuminating the at least one of the subject's eyes with a light.

22. The apparatus of claim 12, wherein the apparatus provides the visual target for the subject.

23. The apparatus of claim 12, wherein the image is captured in response to the power of the one of the subject's eyes being within a predetermined range.

24. The apparatus of claim 12, wherein the memory has further computer-executable instructions stored thereon that, when executed by the processor, cause the processor to adjust the phoria measurement based on the autorefraction measurement.

25. The apparatus of claim 12, wherein the apparatus is a computing device.

26. The apparatus of claim 25, wherein the computing device is a laptop computer, a tablet computer or a mobile phone.

27. The apparatus of claim 12, wherein the light is in a visible or non-visible portion of an electromagnetic spectrum.

* * * * *